United States Patent [19]

Honda

[11] Patent Number: 5,050,198
[45] Date of Patent: Sep. 17, 1991

[54] METHOD AND SYSTEM FOR PROCESSING X-RAY IMAGE IN X-RAY EQUIPMENT

[75] Inventor: Michitaka Honda, Yaita, Japan

[73] Assignee: Kabushiki Kaisha Toshiba, Kawasaki, Japan

[21] Appl. No.: 487,054

[22] Filed: Mar. 5, 1990

[30] Foreign Application Priority Data

Mar. 9, 1989 [JP] Japan .................. 1-57211

[51] Int. Cl.$^5$ .................. H05G 1/64; H04N 5/32
[52] U.S. Cl. .................. 378/99; 378/7; 378/5; 378/186; 378/154; 358/111
[58] Field of Search .................. 378/7, 154, 5, 155, 378/4, 185, 186, 207, 99, 164; 358/111

[56] References Cited

U.S. PATENT DOCUMENTS

| | | | |
|---|---|---|---|
| 4,550,419 | 10/1985 | Aichinger et al. | 358/111 |
| 4,599,742 | 7/1986 | Kikuchi et al. | 378/99 |
| 4,651,002 | 3/1987 | Anno | 378/99 |
| 4,653,080 | 3/1987 | Kikuchi et al. | 378/7 |
| 4,656,650 | 4/1987 | Kikuchi et al. | 378/7 |
| 4,741,009 | 4/1988 | Yamagata et al. | 378/99 |
| 4,823,370 | 4/1989 | Kikuchi | 378/99 |

FOREIGN PATENT DOCUMENTS

0142864 11/1984 European Pat. Off. .
0263210 4/1988 European Pat. Off. .

OTHER PUBLICATIONS

European Search Report Corresponding to EPA 0,142,864.
European Search Report Corresponding to EPA 0,263,210.

Primary Examiner—Edward P. Westin
Assistant Examiner—Don Wong
Attorney, Agent, or Firm—Finnegan, Henderson, Farabow, Garrett, and Dunner

[57] ABSTRACT

In X-ray photography by an X-ray equipment, grid images based on only a grid are acquired by a grid image generating circuit under various photograph conditions, and are stored in image memories. A subject image based on a subject to be examined is acquired under a predetermined photograph condition. A grid image which is acquired under the same photograph condition as that of the subject image or under a condition similar thereto is read out from a corresponding image memory. The subject image and the readout grid image are regulated by gain regulators to have the same gain. The subject image is then divided by the grid image in the divider. As a result, the subject image without the grid image can be obtained.

13 Claims, 4 Drawing Sheets

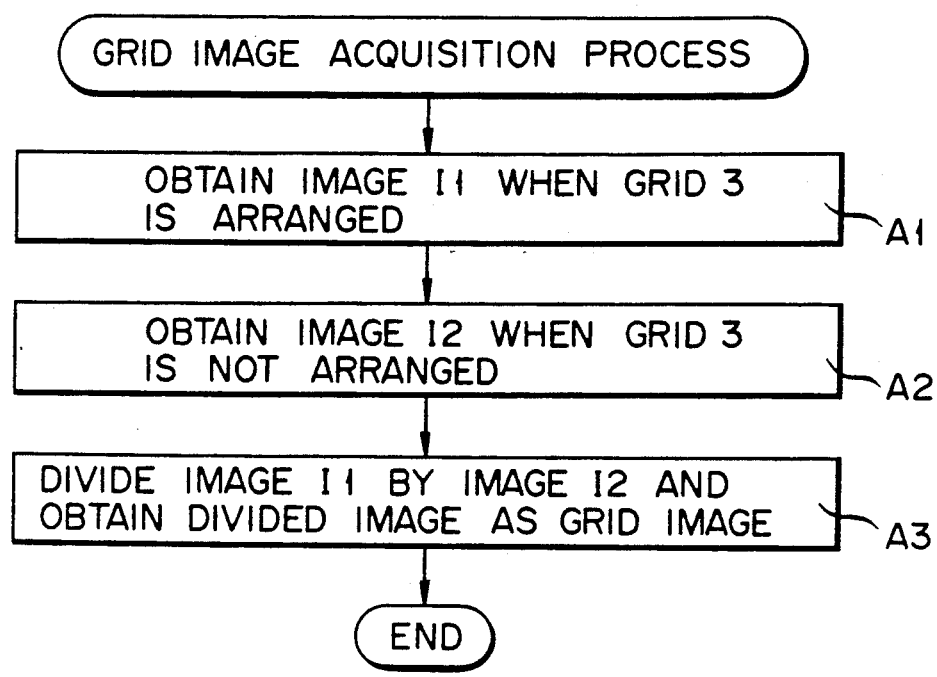
F I G. 2
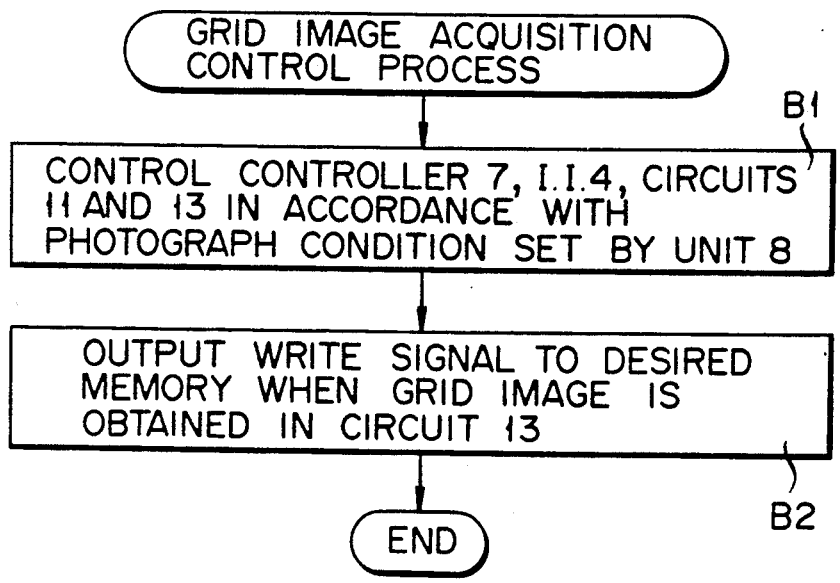
F I G. 3

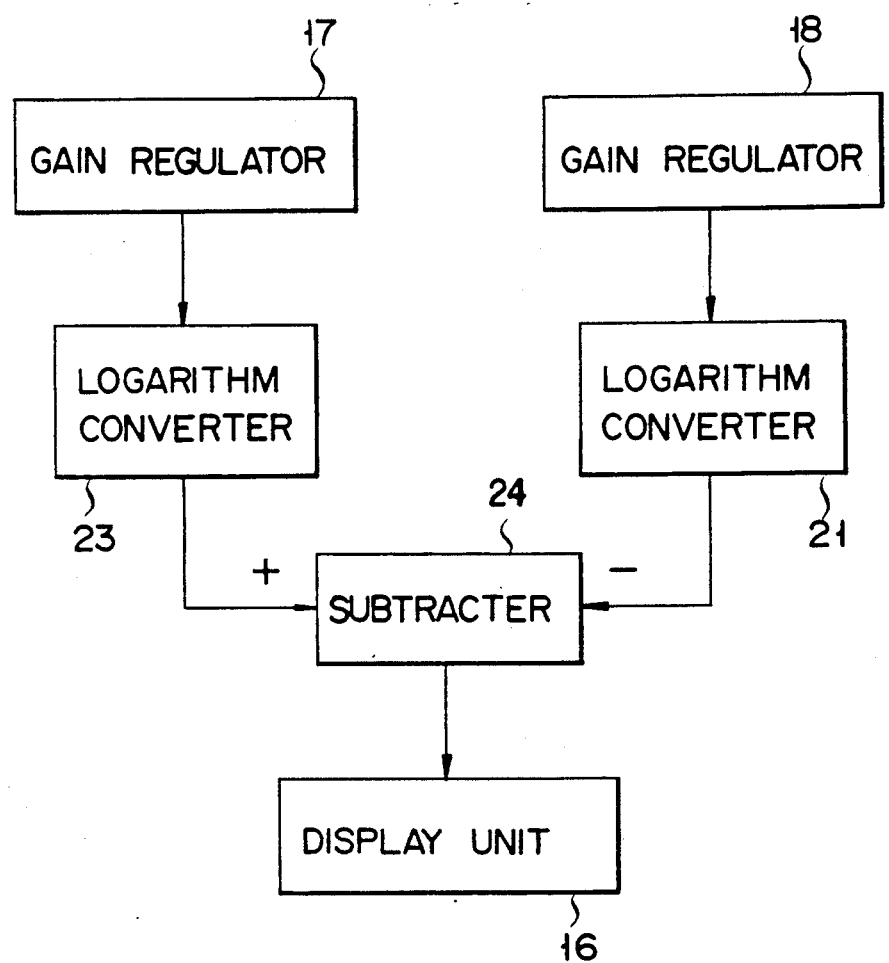
F I G. 5

METHOD AND SYSTEM FOR PROCESSING X-RAY IMAGE IN X-RAY EQUIPMENT

BACKGROUND OF THE INVENTION

1. Field of the Invention

The present invention relates to a method and system for processing X-ray images in an X-ray equipment.

2. Description of the Related Art

In conventional X-ray equipment, X-rays are radiated from an X-ray source as an X-ray tube onto a subject to be examined. The X-rays passed through the subject are converted into light by an image intensifier (I.I.), and the light is incident on an optical system. An X-ray image of the subject is formed by this light. The formed X-ray image is converted into a TV signal by a TV camera and is displayed on a TV monitor. When a predetermined portion of the subject is displayed on the TV monitor, an X-ray image is formed on an X-ray film by further radiating X-rays on the subject.

When the X-rays are passed through the subject, scattered X-rays are superposed on passed X-rays. These scattered X-rays degrade the quality of the X-ray image formed on the X-ray film. In the conventional X-ray equipment, therefore, in order to prevent incidence of scattered X-rays onto an image intensifier, a grid is arranged between a subject and the image intensifier. This grid has a mesh structure and hence can attenuate scattered X-rays which are obliquely radiated onto the image intensifier.

Recently, a CCD (Charge Coupled Device) is used as a TV camera of X-ray equipment. In X-ray photography using a CCD camera, however, the shadow of a grid is formed on an X-ray image. More specifically, if the resolution of the camera is lower than the maximum spatial frequency of a subject to be examined, a phenomenon called aliasing occurs. If a grid having cyclic fine meshes is arranged, a shadow such as moire fringes is formed on an image. Therefore, X-ray diagnostic information is degraded.

Under the circumstances, demands have arisen for an X-ray equipment which can eliminate a grid image formed on an X-ray image.

SUMMARY OF THE INVENTION

It is an object of the present invention to provide a method and system for processing X-ray images in X-ray equipment.

According to one aspect of the present invention, there is provided a method for processing X-ray images in X-ray equipment, the method comprising the steps of:

acquiring a plurality of grid images in accordance with a plurality of grid image photograph conditions;

storing the acquired grid images;

acquiring a subject image in accordance with a subject image photograph condition;

comparing the subject image photograph condition with the grid image photograph conditions;

reading out one of the stored grid images in accordance with the comparison result; and dividing the acquired subject image by the read out grid image.

According to another aspect of the present invention, there is provided a system for processing X-ray images in an X-ray equipment, the system comprising:

grid image acquiring means for acquiring a plurality of grid images in accordance with a plurality of grid image photograph conditions;

storing means for storing the plurality of grid images;

subject image acquiring means for acquiring a subject image in accordance with a subject image photograph condition;

comparing means for comparing the subject image photograph condition with the grid image photograph conditions; and dividing means for dividing the subject image by one of the stored grid images in accordance with the comparison result.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 2 is a flow chart for explaining an operation of a grid image generating circuit of the system;

FIGS. 3 and 4 are flow charts for explaining an operation of a process and control unit of the system; and FIG. 5 is a block diagram showing a modification of the system.

DETAILED DESCRIPTION OF THE PREFERRED EMBODIMENTS

An embodiment of the present invention will be described below with the accompanying drawings.

Figure 1:
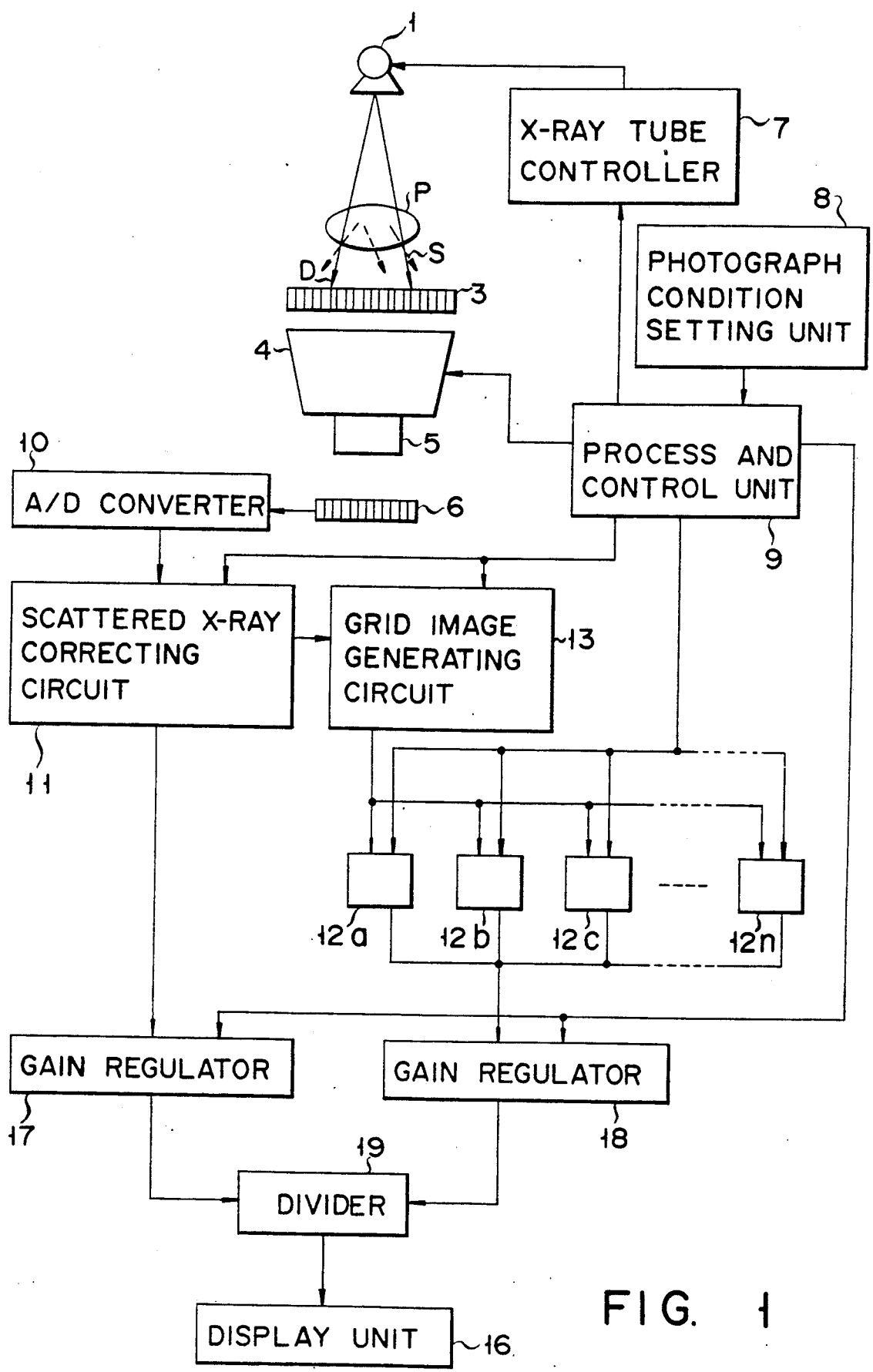
FIG. 1 is a block diagram showing an arrangement of a system according to an embodiment of the present invention.

In FIG. 1, the system comprises an X-ray tube 1, a grid 3, an image intensifier (to be referred to as an I.I. hereinafter) 4, an optical system 5, a TV camera 6, an X-ray tube controller 7, a photograph condition setting unit 8, a process and control unit 9, an A/D converter 10, a scattered X-ray correcting circuit 11, image memories 12a to 12n, a grid image generating circuit 13, a display unit 16, gain regulators 17 and 18, and a divider 19.

The X-ray tube 1 is used as an X-ray source for radiating X-rays on a subject P to be examined.

The grid 3 is arranged to pass direct X-rays D and not to pass scattered X-rays S. An X-ray image I obtained by X-ray photography is represented by the following equation:

$$I = Pa \cdot g + Sa \qquad (1)$$

where Pa is a subject image obtained by only the direct X-rays D without using the grid 3, g is a grid factor and corresponds to a grid image obtained by the direct X-rays D passed through the grid 3, and Sa is a scattered X-ray image obtained by the scattered X-rays using the grid 3.

Since lead slits are regularly arranged in the grid 3, the direct X-rays D are intercepted by the lead slits, and spatially cyclic modulation is performed.

U.S. Pat. Nos. 4,599,742, 4,653,080, 4656,650, and 4,823,370 disclose methods of correcting the subject image Pa having the scattered X-ray image Sa, thereby estimating the scattered X-ray image. As is apparent from equation (1), therefore, the subject image Pa can be acquired by removing the scattered X-ray image Sa from the X-ray image I and dividing the resultant image by the grid image g.

The I.I. 4 converts the X-rays passed through the grid 3 into light. This light is input to the TV camera through the optical system 5, and is converted into a TV signal.

The A/D converter 10 converts the TV signal from the TV camera 6 into a digital signal.

The scattered X-ray correcting circuit 11 corrects the scattered X-ray image Sa on the basis of the digital signal from the A/D converter 10, and acquires a corrected subject image Pa·g and a corrected grid image Aa·g.

The grid image generating circuit 13 acquires the grid image g in accordance with a flow chart shown in FIG. 2.

In step A1, when the grid 3 is arranged without the subject P, a corrected grid image I1 is acquired by the following equation:

$$I1 = Aa \cdot g \quad (2)$$

In step A2, an image I2 obtained without the subject P and the grid 3 is acquired by the following equation:

$$I2 = Aa \quad (3)$$

In step A3, the image I1 is divided by the image I2, and this divided image is obtained as the grid image g according to equations (2) and (3).

The photograph condition setting unit 8 sets photograph conditions for obtaining the grid image g.

The image memories 12a to 12n store the grid image acquired by the grid image generating circuit 13 and the photograph conditions.

Of the photograph conditions, an I.I. size is important. As the I.I. size, for example, 6"/9"/12" are selected. Grid images obtained on the basis of these sizes are respectively stored in the image memories 12a to 12n. Since the tube voltage of the X-ray tube 1 is associated with the X-ray transmittance of an interspacer of the grid 3, the tube voltage of the X-ray tube 1 may be used as a photograph condition.

The gain regulators 17 and 18 regulate the corrected subject image Pa·g acquired by the scattered X-ray correcting circuit 11 and the grid image g read out from the image memories 12a to 12n to have the same gain.

The divider 19 divides the corrected subject image Pa·g by the grid image g, and performs inverse logarithm conversion of the subject image Pa.

The display unit 16 displays the subject image obtained by the divider 19.

The process and control unit 9 controls the I.I. 4, the X-ray tube controller 7, the scattered X-ray correcting circuit 11, the grid image generating circuit 13, the image memories 12a to 12n, and the gain regulators 17 and 18 in accordance with the photograph condition set by the photograph condition setting unit 8.

An operation of the system of the embodiment will be described below.

As described above, X-ray images are acquired when the subject P is not arranged, with and without the grid 3, respectively. In this case, in order to acquire the grid image g, the process and control unit 9 is operated in accordance with a flow chart shown in FIG. 3.

In step B1, the X-ray tube controller 7, the I.I. 4, the scattered X-ray correcting circuit 11, and the grid image generating circuit 13 are controlled in accordance with a photograph condition set by the photograph condition setting unit 8.

With this control, an X-ray radiation signal is input from the X-ray tube controller 7 to the X-ray tube 1, and X-rays are generated. The images I1 and I2 with and without the grid 3 are acquired. As described above, these images are processed by the grid image generating circuit 13 so as to acquire only the grid image g.

In step B2, if the grid image g is acquired by the grid image generating circuit 13, a write signal is output to cause a predetermined memory of the image memories 12a to 12n to store the grid image g.

In the above-described manner, the grid image g is calculated by equations (2) and (3) for each size of the I.I. 4 as a photograph condition, and is stored in the image memories 12a to 12n. If an X-ray focal size is used as a photograph condition, the grid image g is stored in the image memories 12a to 12n for each X-ray focal size. In addition, if the tube voltage of the X-ray tube 1 is used as a photograph condition, the grid image g is stored in the image memories 12a to 12n for each tube voltage.

Figure 4:
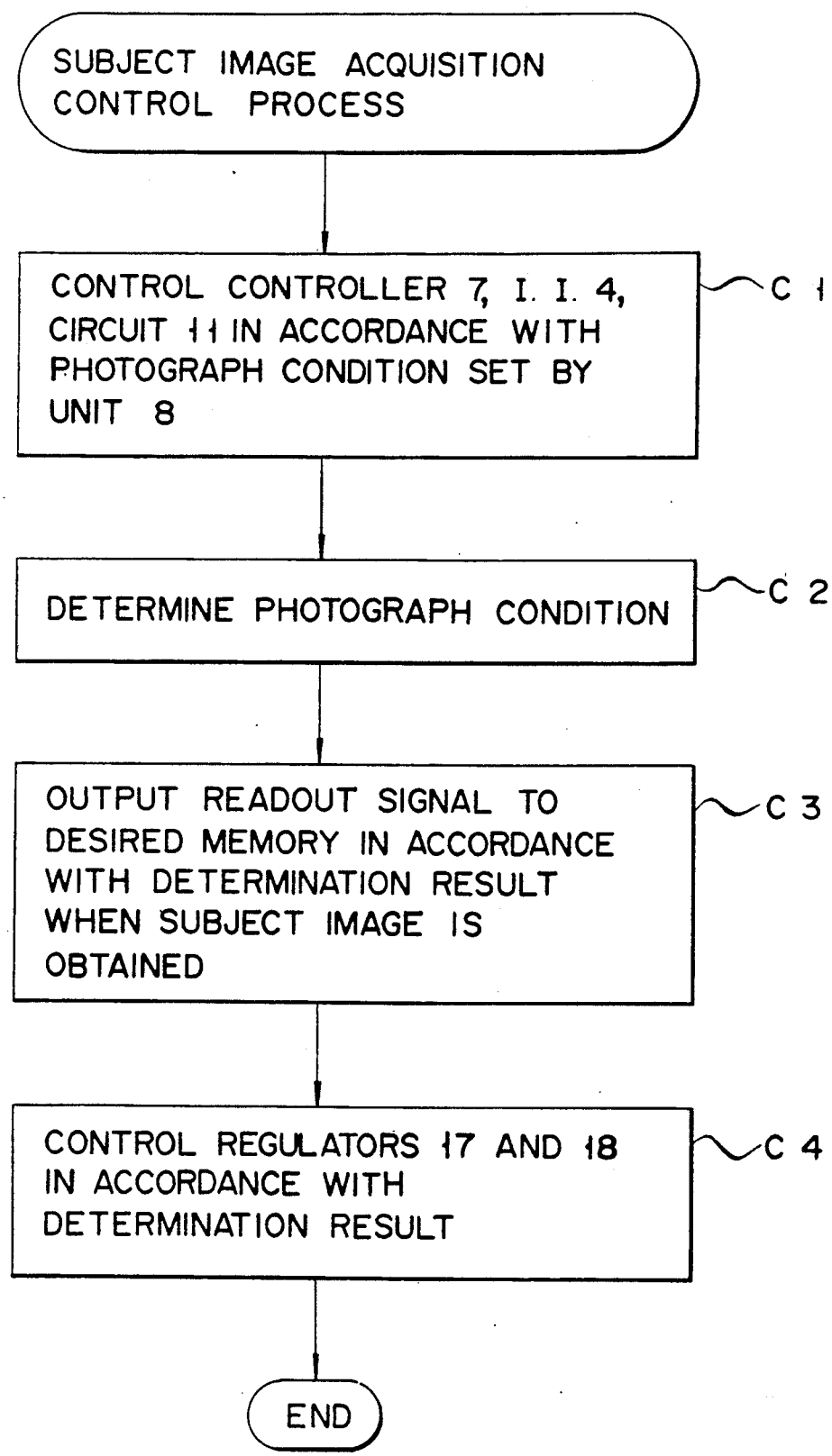

Subsequently, in order to acquire the subject image Pa by X-ray photography when the subject P is arranged, the process and control unit 9 is operated in accordance with a flow chart shown in FIG. 4.

In step C1, the X-ray tube controller 7, the I.I. 4, and the scattered X-ray correcting circuit 11 are controlled in accordance with the photograph condition set by the photograph condition setting unit 8.

With this control, an X-ray radiation signal is input from the X-ray tube controller 7 to the X-ray tube 1 so as to radiate X-rays onto the subject P. The X-rays are incident on the I.I. 4 through the subject P and the grid 3, and are converted into light. This light is converted into a TV signal by the TV camera 6 through the optical system 5. The TV signal is converted into a digital signal by the A/D converter 10 and is input to the scattered X-ray correcting circuit 11 The scattered X-ray image Sa corresponding to the digital signal is corrected by the scattered X-ray correcting circuit 11. With this operation, the corrected subject image Pa·g is obtained.

In step C2, the set photograph condition is determined to specify a grid image g which is obtained by the same photograph condition as that of the subject image P or a condition most similar thereto.

In step C3, if the corrected subject image Pa·g is acquired, a readout signal is output to read out the grid image g from a predetermined image memory of the image memories 12a to 12n in accordance with the determination result in step C2.

In step C4, the gain regulators 17 and 18 are controlled in accordance with the determination result in step C2. With this control, the grid image g and the corrected subject image Pa·g which are input to the gain regulators 17 and 18 are regulated to have the same gain.

Note that the corrected subject image Pa·g is divided by the grid image g and is subjected to inverse logarithm conversion in the divider 19. The subject image P is displayed on the display unit 16.

As described above, according to the embodiment, the grid images g based on the respective photograph conditions are acquired in advance and are stored in the image memories 12a to 12n. After X-ray photography with respect to the subject P, a grid image g acquired by the same photograph condition as that of the subject image P or a condition similar thereto is read out from a corresponding one of the image memories 12a to 12n, and the corrected subject image Pa·g is divided by the readout grid image g. That is, since the grid image g is removed from the corrected subject image Pa·g, moire fringes formed by the grid 3 can be eliminated. In addition, even if a photograph condition at the grid 3 is different from that at the subject P, proper correction can be performed. Therefore, if a CCD camera is used, an image can be acquired without aliasing. Hence, the image quality can be improved.

The particular embodiment of the present invention has been described above. However, the present invention is not limited to this. For example, as shown in FIG. 5, logarithm converters 23 and 21 are arranged between gain regulators 17 and 18 and divider 19. With this arrangement, after the gain-regulation, the corrected subject image Pa·g and grid image g are respectively logarithm-converted by the logarithm converters 23 and 21, and are subtracted by the subtracter 24.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method for processing X-ray images in X-ray equipment, the method comprising the steps of:
   acquiring a plurality of grid images in accordance with a plurality of grid image photograph conditions;
   storing the acquired grid images;
   acquiring a subject image in accordance with a subject image photograph condition;
   comparing the subject image photograph condition with the grid image photograph conditions;
   reading out one of the stored grid images in accordance with the comparison result; and dividing the acquired subject image by the read out grid image.

2. The method according to claim 1, wherein the dividing step includes the step of regulating a first gain concerning the subject image and a second gain concerning the read out grid image when the grid image photograph condition corresponding to the read out grid image differs from the subject image photograph condition.

3. The method according to claim 1, wherein each of the grid image photograph conditions and the subject image photograph conditions include one of an X-ray tube voltage and an X-ray focal size.

4. The method according to claim 3, wherein condition data representing the grid image photograph conditions are stored with the grid images.

5. The method according to claim 3, wherein the step of acquiring the plurality of grid images includes the steps of:
   setting a grid image photograph condition;
   arranging a grid into the X-ray equipment;
   obtaining a grid image in accordance with the set grid image photograph condition;
   removing the arranged grid from the X-ray equipment;
   obtaining an image of no object in accordance with the set grid image photograph condition; and
   dividing the grid image by the image of no object.

6. A system for processing X-ray images in X-ray equipment, the system comprising:
   grid image acquiring means for acquiring a plurality of grid images in accordance with a plurality of grid image photograph conditions;
   storing means for storing the plurality of grid images;
   subject image acquiring means for acquiring a subject image in accordance with a subject image photograph condition;
   comparing means for comparing the subject image photograph condition with the grid image photograph condition; and
   dividing means for dividing the subject image by one of the stored grid images in accordance with the comparison result.

7. The system according to claim 6, wherein each of the grid image photograph conditions and the subject image photograph conditions include one of an x-ray tube voltage and an X-ray focal size.

8. The system according to claim 7, wherein the dividing means includes means for regulating a first gain concerning the subject image and a second gain concerning the one of the grid images when the grid image photograph condition corresponding to the one of the grid images differs from the subject image photograph condition.

9. The system according to claim 7, wherein condition data representing the grid image photograph conditions are stored with the grid images in the storing means.

10. A system for processing X-ray images in X-ray equipment, the system comprising:
    grid image acquiring means for acquiring a grid image in accordance with a grid image photograph condition;
    storing means for storing the grid image;
    subject image acquiring means for acquiring a subject image in accordance with a subject image photograph condition; and
    dividing means for dividing the subject image by the stored grid image.

11. The system according to claim 10, wherein each of the grid image photograph conditions and the subject image photograph conditions include one of an image intensifier size, an X-ray tube voltage and an X-ray focal size.

12. The system according to claim 11, wherein the dividing means includes means for regulating a first gain concerning the subject image and a second gain concerning the grid image.

13. The system according to claim 11, wherein condition data representing the grid image photograph condition is stored with the grid image in the storing means.

* * * * *